(12) United States Patent
Kumar et al.

(10) Patent No.: US 12,354,711 B2
(45) Date of Patent: Jul. 8, 2025

(54) METHODS AND SYSTEMS FOR SCREENING AND DESIGN OF CORROSION INHIBITORS

(71) Applicant: Tata Consultancy Services Limited, Mumbai (IN)

(72) Inventors: Dharmendr Kumar, Pune (IN); Beena Rai, Pune (IN); Abhishek Agarwal, Pune (IN); Vinay Jain, Pune (IN)

(73) Assignee: TATA CONSULTANCY SERVICES LIMITED, Mumbai (IN)

(*) Notice: Subject to any disclaimer, the term of this patent is extended or adjusted under 35 U.S.C. 154(b) by 419 days.

(21) Appl. No.: 18/102,171

(22) Filed: Jan. 27, 2023

(65) Prior Publication Data

US 2023/0282315 A1 Sep. 7, 2023

(30) Foreign Application Priority Data

Mar. 4, 2022 (IN) .............................. 202221011898

(51) Int. Cl.
| | |
|---|---|
| *G16C 20/10* | (2019.01) |
| *G16C 20/20* | (2019.01) |
| *G16C 20/70* | (2019.01) |

(52) U.S. Cl.
CPC ............. *G16C 20/10* (2019.02); *G16C 20/20* (2019.02); *G16C 20/70* (2019.02)

(58) Field of Classification Search
CPC ........ G16C 20/10; G16C 20/20; G16C 20/62; G16C 20/64
See application file for complete search history.

(56) References Cited

U.S. PATENT DOCUMENTS

| | | | |
|---|---|---|---|
| 2017/0137634 A1* | 5/2017 | Balasubramanian | ....................... C23F 11/173 |
| 2018/0312980 A1* | 11/2018 | Crawford | ................ C23F 11/04 |
| 2020/0176088 A1* | 6/2020 | Kanamarlapudi | ..... G16C 20/70 |

OTHER PUBLICATIONS

Edoziuno et al., "Optimization and development of predictive models for the corrosion inhibition of mild steel in sulphuric acid by methyl-5-benzoyl-2-benzimidazole carbamate (mebendazole)," Cogent Engineering, 7:1714100 (2020).

(Continued)

*Primary Examiner* — Lam S Nguyen
(74) *Attorney, Agent, or Firm* — Finnegan, Henderson, Farabow, Garrett & Dunner, LLP

(57) ABSTRACT

This disclosure relates generally to methods and systems for screening and design of corrosion inhibitors. Conventional techniques in the art for predicting the inhibition efficiency of the molecule are not so accurate, where the inhibition efficiency is one of the important parameter for screening and design of corrosion inhibitors. In the present disclosure, the IE prediction model is developed by training a multi-task network model using the molecular descriptors of different classes of the molecules, and also the experimental conditions of the molecule. Further, a unique screening technique is disclosed that screens the molecules using various parameters including the inhibition efficiency of the molecule, an energy gap of the molecule, a synergistic effect of the molecules and an interaction energy of the molecules. Further the present disclosure allows to design a new molecule by making changes to the molecules that suits based on the end applications.

17 Claims, 7 Drawing Sheets

(56) References Cited

OTHER PUBLICATIONS

Schiessler et al., "Predicting the inhibition efficiencies of magnesium dissolution modulators using sparse machine learning models," Nature Partner Journals (2021).
Winkler et al., "Towards chromate-free corrosion inhibitors: structure-property models for organic alternatives," Green Chem., 16:3349-3357 (2014).

* cited by examiner

METHODS AND SYSTEMS FOR SCREENING AND DESIGN OF CORROSION INHIBITORS

PRIORITY CLAIM

This U.S. patent application claims priority under 35 U.S.C. § 119 to: Indian Patent Application No. 202221011898, filed on Mar. 4, 2022. The entire contents of the aforementioned application are incorporated herein by reference.

TECHNICAL FIELD

The disclosure herein generally relates to the field of corrosion inhibitors, and, more particularly, to methods and systems for screening and design of corrosion inhibitors.

BACKGROUND

Corrosion of metallic structures is a ubiquitous problem in various industries such as power generation, oil and gas, pulp and paper, metals processing etc. The corrosion results in significant financial losses. Use of corrosion inhibitors is one of the most effective and economical ways to mitigate corrosion of metal and alloy components. The corrosion inhibitors are substances that are added in small quantities in corrosive media to protect metal and alloy components from the corrosion. The corrosion inhibitors are typically surfactant-type compounds comprising (i) a hydrophilic head group containing heteroatoms such as Oxygen (O), Nitrogen (N), and Sulphur (S), and (ii) a hydrophobic tail group comprising hydrocarbon groups. These compounds form an effective barrier layer on the metal or alloy surface thereby stopping the transport of ions and corrosive species thus, inhibiting the corrosion. However, the conventional corrosion inhibitors and their formulations are toxic and non-biodegradable in nature. Therefore, effective corrosion inhibitors that meet environmental regulations are of high importance.

To develop new corrosion inhibitors, experimental approaches, molecular modelling as well as machine learning based approaches are extensively utilized in the art. The experiments, however, are usually time-consuming and expensive. Computer simulation based molecular modelling approaches such as a density functional theory and molecular dynamics have gained popularity due to the increase in available computational power. However, these approaches still take long time and as such may not be used for screening a large number of molecules for developing potential corrosion inhibitors. Further, molecular modelling techniques may not predict new and effective corrosion inhibitors with high accuracy as they cannot simulate various materials with realistic chemical composition (e.g. steel).

Most of the conventional machine learning based techniques are used to predict the corrosion inhibition efficiency of molecules, and new corrosion inhibitor molecules are screened based on the predicted inhibition efficiency. However, the datasets used for training the models are very small and limited to a single class of compounds (i.e. lacked chemical diversity). Thus, the trained models may not be efficient for are screening the new compounds from other classes.

SUMMARY

Embodiments of the present disclosure present technological improvements as solutions to one or more of the above-mentioned technical problems recognized by the inventors in conventional systems.

In an aspect, a processor-implemented method for screening and design of corrosion inhibitors is provided. The method including the steps of: receiving a plurality of corrosion inhibitor molecules from a molecular structure database, and one or more experimental conditions for each of the plurality of corrosion inhibitor molecules from an experimental repository; determining one or more quantum chemical descriptors for each of the plurality of corrosion inhibitor molecules, using a quantum chemical descriptors calculating technique; determining one or more molecular descriptors for each of the plurality of corrosion inhibitor molecules, using a molecular descriptors calculating technique; predicting an inhibition efficiency (IE) for each of the plurality of corrosion inhibitor molecules, based on (i) the one or more molecular descriptors, and (ii) the one or more experimental conditions, using an IE prediction model; determining an energy gap for each of the plurality of corrosion inhibitor molecules, based on the one or more quantum chemical descriptors for each of the plurality of corrosion inhibitor molecules; identifying out of the plurality of corrosion inhibitor molecules, (i) a first set of corrosion inhibitor molecules having the IE greater than or equal to a predefined IE threshold, and (ii) a second set of corrosion inhibitor molecules having the IE less than the predefined IE threshold, and adding the first set of corrosion inhibitor molecules to a potential corrosion inhibitor molecules repository; identifying, out of the plurality of corrosion inhibitor molecules, (i) a third set of corrosion inhibitor molecules having the energy gap greater than a predefined energy gap threshold, and (ii) a fourth set of corrosion inhibitor molecules having the energy gap less than or equal to the predefined energy gap threshold; forming one or more first corrosion inhibitor molecule pairs from (i) the second set of corrosion inhibitor molecules, and (ii) the third set of corrosion inhibitor molecules; identifying one or more second corrosion inhibitor molecule pairs that satisfies a synergy criteria out of the one or more first corrosion inhibitor molecule pairs, and to add remaining first corrosion inhibitor molecule pairs to a corrosion inhibitor molecules modification repository; determining an interaction energy for (i) each corrosion inhibitor molecule present in the fourth set of corrosion inhibitor molecules, and (ii) each corrosion inhibitor molecule pair present in the one or more second corrosion inhibitor molecule pairs; adding each corrosion inhibitor molecule present in (i) the fourth set of corrosion inhibitor molecules, and (ii) the one or more second corrosion inhibitor molecule pairs, to one of: (i) the potential corrosion inhibitor molecules repository and (ii) the corrosion inhibitor molecules modification repository, based on the corresponding interaction energy; identifying a first optimal corrosion inhibitor molecule out of the one or more corrosion inhibitor molecules present in the potential corrosion inhibitor molecules repository, based on a feasibility criteria, to perform an experimental synthesis on the first optimal corrosion inhibitor molecule, and to add remaining one or more corrosion inhibitor molecules present in the potential corrosion inhibitor molecules repository to the corrosion inhibitor molecules modification repository; identifying a second optimal corrosion inhibitor molecule out of the one or more corrosion inhibitor molecules present in the corrosion inhibitor molecules modification repository, based on the feasibility criteria; performing modifications to the second optimal corrosion inhibitor molecule, to obtain a modified corrosion inhibitor molecule, and adding the modified corrosion inhibitor molecule to the plurality of corrosion inhibitor molecules, for further screening and design of corrosion inhibitors; and performing plant trails on the first optimal corrosion inhibitor molecule.

In another aspect, a system for screening and design of corrosion inhibitors is provided. The system includes: a memory storing instructions; one or more Input/Output (I/O) interfaces; and one or more hardware processors coupled to the memory via the one or more I/O interfaces, wherein the one or more hardware processors are configured by the instructions to: receive a plurality of corrosion inhibitor molecules from a molecular structure database, and one or more experimental conditions for each of the plurality of corrosion inhibitor molecules from an experimental repository; determine one or more quantum chemical descriptors for each of the plurality of corrosion inhibitor molecules, using a quantum chemical descriptors calculating technique; determine one or more molecular descriptors for each of the plurality of corrosion inhibitor molecules, using a molecular descriptors calculating technique; predict an inhibition efficiency (IE) for each of the plurality of corrosion inhibitor molecules, based on (i) the one or more molecular descriptors, and (ii) the one or more experimental conditions, using an IE prediction model; determine an energy gap for each of the plurality of corrosion inhibitor molecules, based on the one or more quantum chemical descriptors for each of the plurality of corrosion inhibitor molecules; identify, out of the plurality of corrosion inhibitor molecules, (i) a first set of corrosion inhibitor molecules having the IE greater than or equal to a predefined IE threshold, and (ii) a second set of corrosion inhibitor molecules having the IE less than the predefined IE threshold, and adding the first set of corrosion inhibitor molecules to a potential corrosion inhibitor molecules repository; identify, out of the plurality of corrosion inhibitor molecules, (i) a third set of corrosion inhibitor molecules having the energy gap greater than a predefined energy gap threshold, and (ii) a fourth set of corrosion inhibitor molecules having the energy gap less than or equal to the predefined energy gap threshold; form one or more first corrosion inhibitor molecule pairs from (i) the second set of corrosion inhibitor molecules, and (ii) the third set of corrosion inhibitor molecules; identify one or more second corrosion inhibitor molecule pairs that satisfies a synergy criteria, out of the one or more first corrosion inhibitor molecule pairs, and add remaining first corrosion inhibitor molecule pairs to a corrosion inhibitor molecules modification repository; determine an interaction energy for (i) each corrosion inhibitor molecule present in the fourth set of corrosion inhibitor molecules, and (ii) each corrosion inhibitor molecule pair present in the one or more second corrosion inhibitor molecule pairs; add each corrosion inhibitor molecule present in (i) the fourth set of corrosion inhibitor molecules, and (ii) the one or more second corrosion inhibitor molecule pairs, to one of: (i) the potential corrosion inhibitor molecules repository and (ii) the corrosion inhibitor molecules modification repository, based on the corresponding interaction energy; identify a first optimal corrosion inhibitor molecule out of the one or more corrosion inhibitor molecules present in the potential corrosion inhibitor molecules repository, based on a feasibility criteria, to perform an experimental synthesis on the first optimal corrosion inhibitor molecule, and to add remaining one or more corrosion inhibitor molecules present in the potential corrosion inhibitor molecules repository to the corrosion inhibitor molecules modification repository; identify a second optimal corrosion inhibitor molecule out of the one or more corrosion inhibitor molecules present in the corrosion inhibitor molecules modification repository, based on the feasibility criteria; perform modifications to the second optimal corrosion inhibitor molecule, to obtain a modified corrosion inhibitor molecule, and adding the modified corrosion inhibitor molecule to the plurality of corrosion inhibitor molecules, for further screening and design of corrosion inhibitors; and perform plant trails on the first optimal corrosion inhibitor molecule.

In yet another aspect, there is provided one or more non-transitory machine-readable information storage mediums comprising one or more instructions which when executed by one or more hardware processors cause: receiving a plurality of corrosion inhibitor molecules from a molecular structure database, and one or more experimental conditions for each of the plurality of corrosion inhibitor molecules from an experimental repository; determining one or more quantum chemical descriptors for each of the plurality of corrosion inhibitor molecules, using a quantum chemical descriptors calculating technique; determining one or more molecular descriptors for each of the plurality of corrosion inhibitor molecules, using a molecular descriptors calculating technique; predicting an inhibition efficiency (IE) for each of the plurality of corrosion inhibitor molecules, based on (i) the one or more molecular descriptors, and (ii) the one or more experimental conditions, using an IE prediction model; determining an energy gap for each of the plurality of corrosion inhibitor molecules, based on the one or more quantum chemical descriptors for each of the plurality of corrosion inhibitor molecules; identifying, out of the plurality of corrosion inhibitor molecules, (i) a first set of corrosion inhibitor molecules having the IE greater than or equal to a predefined IE threshold, and (ii) a second set of corrosion inhibitor molecules having the IE less than the predefined IE threshold, and adding the first set of corrosion inhibitor molecules to a potential corrosion inhibitor molecules repository; identifying, out of the plurality of corrosion inhibitor molecules, (i) a third set of corrosion inhibitor molecules having the energy gap greater than a predefined energy gap threshold, and (ii) a fourth set of corrosion inhibitor molecules having the energy gap less than or equal to the predefined energy gap threshold; forming one or more first corrosion inhibitor molecule pairs from (i) the second set of corrosion inhibitor molecules, and (ii) the third set of corrosion inhibitor molecules; identifying one or more second corrosion inhibitor molecule pairs that satisfies a synergy criteria, out of the one or more first corrosion inhibitor molecule pairs, and add remaining first corrosion inhibitor molecule pairs to a corrosion inhibitor molecules modification repository; determining an interaction energy for (i) each corrosion inhibitor molecule present in the fourth set of corrosion inhibitor molecules, and (ii) each corrosion inhibitor molecule pair present in the one or more second corrosion inhibitor molecule pairs; adding each corrosion inhibitor molecule present in (i) the fourth set of corrosion inhibitor molecules, and (ii) the one or more second corrosion inhibitor molecule pairs, to one of: (i) the potential corrosion inhibitor molecules repository and (ii) the corrosion inhibitor molecules modification repository, based on the corresponding interaction energy; identifying a first optimal corrosion inhibitor molecule out of the one or more corrosion inhibitor molecules present in the potential corrosion inhibitor molecules repository, based on a feasibility criteria, to perform an experimental synthesis on the first optimal corrosion inhibitor molecule, and to add remaining one or more corrosion inhibitor molecules present in the potential corrosion inhibitor molecules repository to the corrosion inhibitor molecules modification repository; identifying a second optimal corrosion inhibitor molecule out of the one or more corrosion inhibitor molecules present in the corrosion inhibitor molecules modification repository, based on the feasibility criteria; performing modifications to the second optimal corrosion inhibitor molecule, to obtain a modified corrosion inhibitor molecule, and adding the modified corrosion inhibitor molecule to the plurality of corrosion inhibitor molecules, for further screening and design of corrosion inhibitors; and performing plant trails on the first optimal corrosion inhibitor molecule.

In an embodiment, the modifications performed to the second optimal corrosion inhibitor molecule, to obtain the modified corrosion inhibitor molecule, by: determining xyz-coordinates of the second optimal corrosion inhibitor molecule using a coordinates determination model; identifying one or more locations having atoms for the second optimal corrosion inhibitor molecule where the modifications to be performed, based on the xyz-coordinates; replacing an atom present in each location of the one or more locations in the second optimal corrosion inhibitor molecule, with a functional group identified from one or more functional groups; and rotating and adjusting the replaced functional groups in the second optimal corrosion inhibitor molecule in such a way that a distance between the atoms of the replaced functional groups and the existing atoms in the second optimal corrosion inhibitor molecule should be greater than a sum of covalent radii of the atoms, to obtain the modified corrosion inhibitor molecule.

In an embodiment, the IE prediction model is obtained by: receiving (i) a plurality of training corrosion inhibitor molecules from the molecular structure database, (ii) a plurality of pre-processed molecular descriptors for each of the plurality of training corrosion inhibitor molecules, (iii) the one or more experimental conditions for each of the plurality of training corrosion inhibitor molecules, from the experimental repository and (iv) the inhibition efficiency (IE) for each of the plurality of training corrosion inhibitor molecules from the experimental repository; and training a multi-task network model comprising an auto-encoder and a prediction network model, with the plurality of training corrosion inhibitor molecules based on a batch size, using (i) the plurality of pre-processed molecular descriptors associated with each training corrosion inhibitor molecule, (ii) the one or more experimental conditions associated with each training corrosion inhibitor molecule, and (iii) the inhibition efficiency (IE) associated with each training corrosion inhibitor molecule, to obtain the IE prediction model, wherein training the multi-task network model with each training corrosion inhibitor molecule comprising: passing a feature vector of the plurality of pre-processed molecular descriptors associated with the training corrosion inhibitor molecule, to an encoder of the auto-encoder, to obtain a latent feature vector of the training corrosion inhibitor molecule; passing the latent feature vector of the training corrosion inhibitor molecule, to a decoder of the auto-encoder, to obtain a reconstructed feature vector associated with the training corrosion inhibitor molecule; concatenating the one or more experimental conditions associated with the training corrosion inhibitor molecule with the latent feature vector of the training corrosion inhibitor molecule, to obtain a concatenated feature vector of the training corrosion inhibitor molecule; passing the concatenated feature vector of the training corrosion inhibitor molecule, to the prediction network model, to obtain a predicted IE associated with the training corrosion inhibitor molecule; minimizing the cost function of the multi-task network model, wherein the cost function is a weighted sum of an auto-encoder cost function and a prediction network model cost function; and updating model weights of the multi-task network model, based on the cost function.

In an embodiment, the auto-encoder cost function is defined as the mean square error between the reconstructed feature vector associated with the training corrosion inhibitor, and the feature vector associated with the training corrosion inhibitor molecule; and the prediction network model cost function is defined as the mean square error between the predicted IE associated with the training corrosion inhibitor molecule, and the IE associated with the training corrosion inhibitor molecule.

In an embodiment, predicting the inhibition efficiency (IE) for each of the plurality of corrosion inhibitor molecules, based on (i) the one or more molecular descriptors, and (ii) the one or more experimental conditions, using the IE prediction model, by; passing a feature vector of the one or more molecular descriptors associated with each of the plurality of corrosion inhibitor molecules, to an encoder of an auto-encoder present in the IE prediction model, to obtain a latent feature vector corresponding to each of the plurality of corrosion inhibitor molecules; concatenating the one or more experimental conditions for each of the plurality of corrosion inhibitor molecules with the latent feature vector corresponding to each of the plurality of corrosion inhibitor molecules, to obtain a concatenated feature vector of each of the plurality of corrosion inhibitor molecules; and passing the concatenated feature vector of each of the plurality of corrosion inhibitor molecules, to a prediction network model present in the IE prediction model, to obtain the inhibition efficiency (IE) for each of the plurality of corrosion inhibitor molecules.

In an embodiment, the one or more experimental conditions are selected from a group comprising but are not limited to: (i) a temperature, (ii) an inhibitor concentration, (iii) an acid concentration, (iv) an alloy composition, (v) a pressure, (vi) a solubility, and (vii) a solution chemistry.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
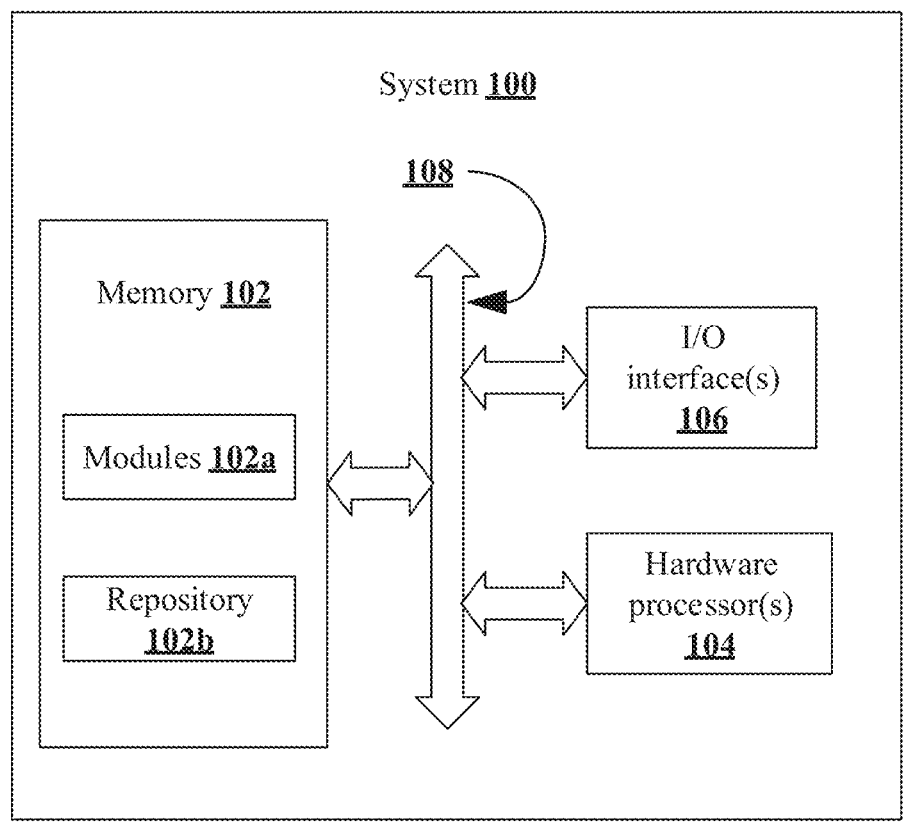
FIG. 1 is an exemplary block diagram of a system for screening and design of corrosion inhibitors, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Corrosion inhibitors are useful to mitigate corrosion of metal or alloy components. However, traditional corrosion inhibitors are toxic and need to be replaced by greener alternatives. Efficient screening models are required to find effective corrosive inhibitor molecules with desired properties. To make these models, database of experimental inhibition efficiency of molecules is essential.

The present disclosure herein provides methods and systems for screening and design of corrosion inhibitors, that addresses the technical problems in the art, by developing an inhibition efficiency (IE) prediction model to predict the IE of the molecule effectively and accurately. The disclosed IE prediction model of the present disclosure is developed by training a multi-task network model using the molecular descriptors of different classes of the molecules, and also the experimental conditions of the molecule. Further, the present disclosure employs a unique screening technique that screens the molecules not only based on the molecular descriptors (for finding the IE), but also using quantum chemical descriptors, and using various parameters including the inhibition efficiency of the molecule, an energy gap of the molecule, a synergistic effect of the molecules and an interaction energy of the molecules. Further the present disclosure allows to design a new molecule by making changes to the molecules that suits based on the end applications.

Referring now to the drawings, and more particularly to FIG. 1 through FIG. 6, where similar reference characters denote corresponding features consistently throughout the figures, there are shown preferred embodiments and these embodiments are described in the context of the following exemplary systems and/or methods.

FIG. 1 is an exemplary block diagram of a system 100 for screening and design of corrosion inhibitors, in accordance with some embodiments of the present disclosure. In an embodiment, the system 100 includes or is otherwise in communication with one or more hardware processors 104, communication interface device(s) or input/output (I/O) interface(s) 106, and one or more data storage devices or memory 102 operatively coupled to the one or more hardware processors 104. The one or more hardware processors 104, the memory 102, and the I/O interface(s) 106 may be coupled to a system bus 108 or a similar mechanism.

The I/O interface(s) 106 may include a variety of software and hardware interfaces, for example, a web interface, a graphical user interface, and the like. The I/O interface(s) 106 may include a variety of software and hardware interfaces, for example, interfaces for peripheral device(s), such as a keyboard, a mouse, an external memory, a plurality of sensor devices, a printer and the like. Further, the I/O interface(s) 106 may enable the system 100 to communicate with other devices, such as web servers and external databases.

The I/O interface(s) 106 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface(s) 106 may include one or more ports for connecting a number of computing systems with one another or to another server computer. Further, the I/O interface(s) 106 may include one or more ports for connecting a number of devices to one another or to another server.

The one or more hardware processors 104 may be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In the context of the present disclosure, the expressions 'processors' and 'hardware processors' may be used interchangeably. In an embodiment, the system 100 can be implemented in a variety of computing systems, such as laptop computers, portable computers, notebooks, hand-held devices, workstations, mainframe computers, servers, a network cloud and the like.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 102 includes a plurality of modules 102*a* and a repository 102*b* for storing data processed, received, and generated by one or more of the plurality of modules 102*a*. The plurality of modules 102*a* may include routines, programs, objects, components, data structures, and so on, which perform particular tasks or implement particular abstract data types.

The plurality of modules 102*a* may include programs or computer-readable instructions or coded instructions that supplement applications or functions performed by the system 100. The plurality of modules 102*a* may also be used as, signal processor(s), state machine(s), logic circuitries, and/or any other device or component that manipulates signals based on operational instructions. Further, the plurality of modules 102*a* can be used by hardware, by computer-readable instructions executed by the one or more hardware processors 104, or by a combination thereof. In an embodiment, the plurality of modules 102*a* can include various sub-modules (not shown in FIG. 1). Further, the memory 102 may include information pertaining to input(s)/output(s) of each step performed by the processor(s) 104 of the system 100 and methods of the present disclosure.

The repository 102*b* may include a database or a data engine. Further, the repository 102*b* amongst other things, may serve as a database or includes a plurality of databases for storing the data that is processed, received, or generated as a result of the execution of the plurality of modules 102*a*. Although the repository 102*a* is shown internal to the system 100, it will be noted that, in alternate embodiments, the repository 102*b* can also be implemented external to the system 100, where the repository 102*b* may be stored within an external database (not shown in FIG. 1) communicatively coupled to the system 100. The data contained within such external database may be periodically updated. For example, data may be added into the external database and/or existing data may be modified and/or non-useful data may be deleted from the external database. In one example, the data may be stored in an external system, such as a Lightweight Directory Access Protocol (LDAP) directory and a Relational Database Management System (RDBMS). In another embodiment, the data stored in the repository 102b may be distributed between the system 100 and the external database.

Figure 2:
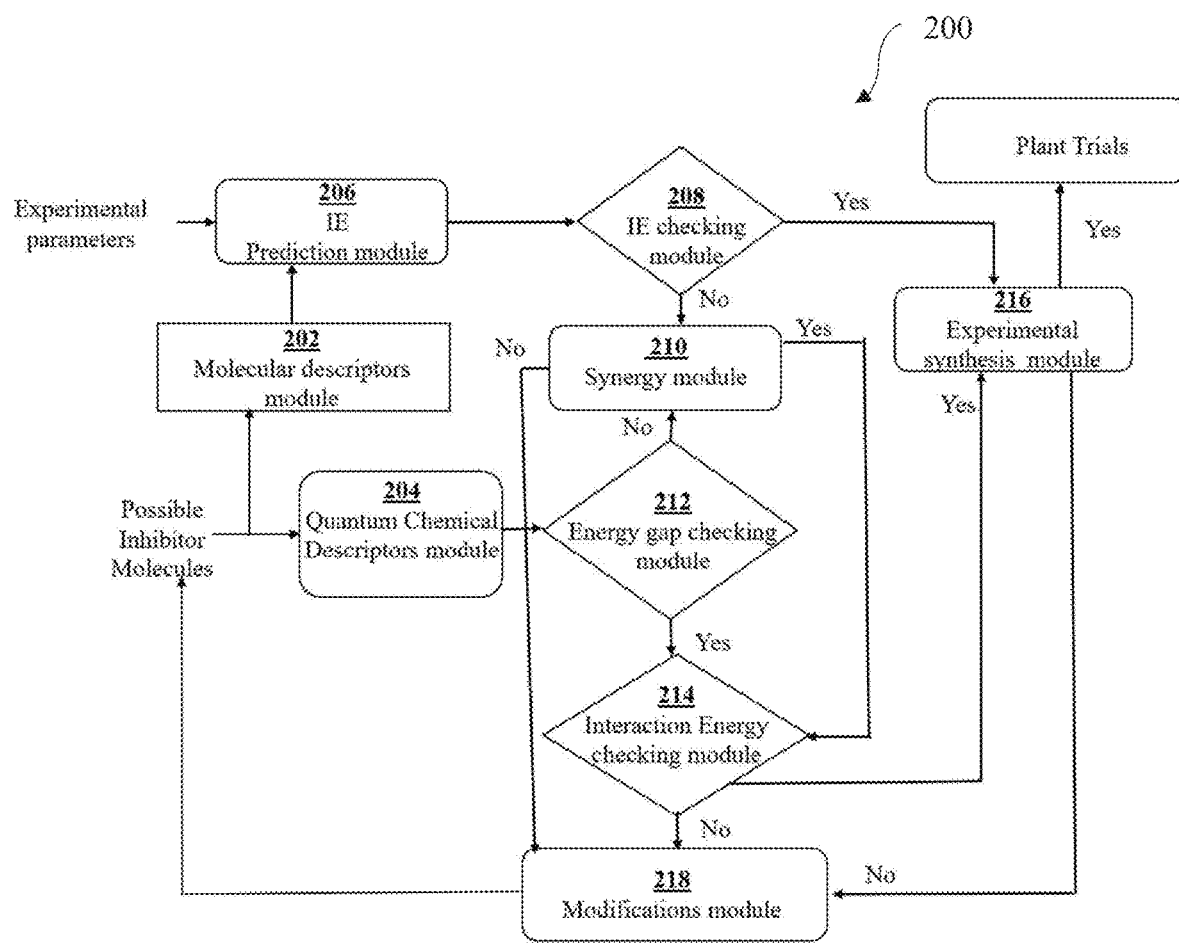
FIG. 2 is an exemplary block diagram illustrating modules of the system of FIG. 1 for screening and design of corrosion inhibitors, in accordance with some embodiments of the present disclosure.
Figure 3A:
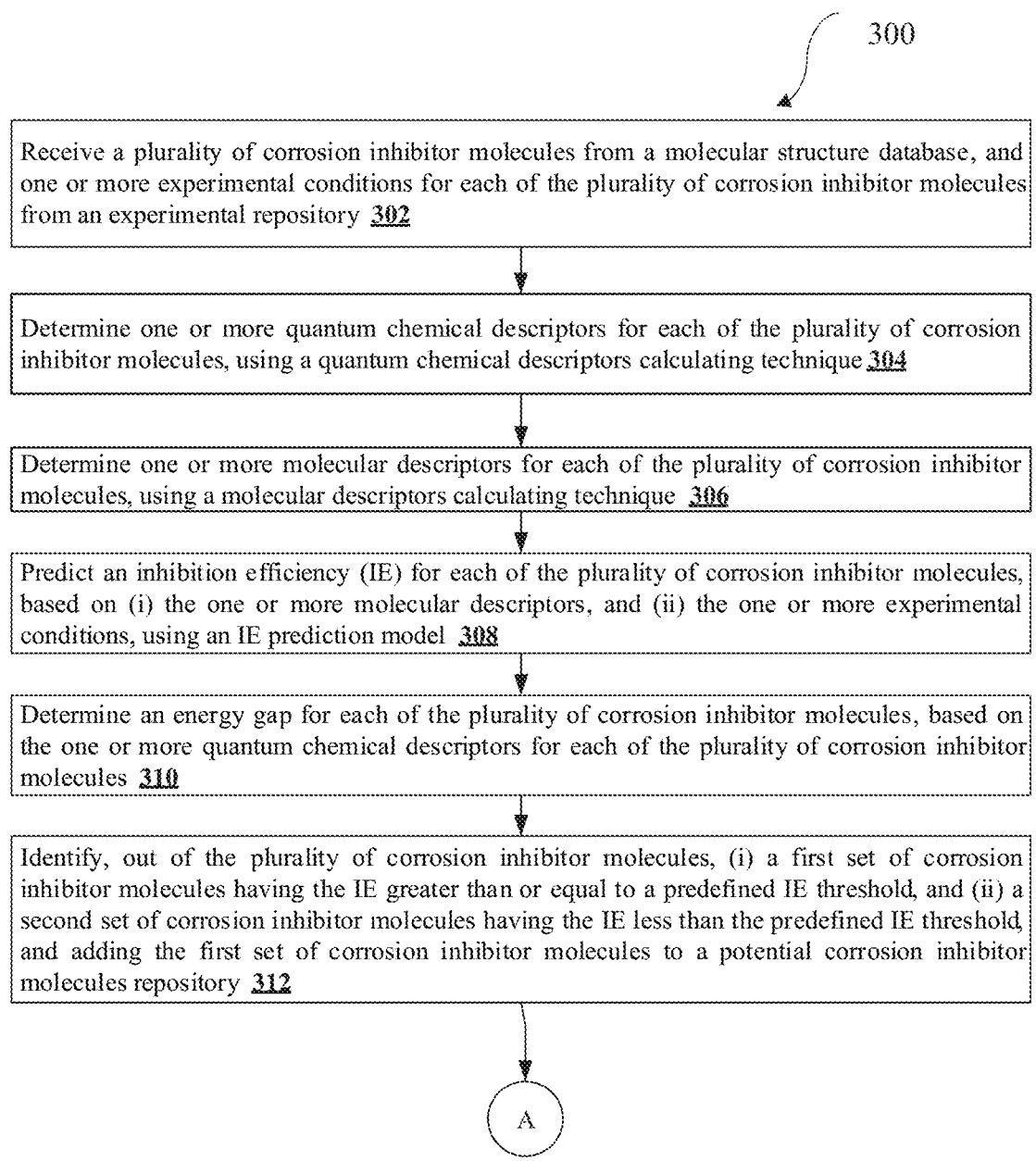
FIG. 3A and FIG. 3B illustrates exemplary flow diagrams of a processor-implemented method for screening and design of corrosion inhibitors, in accordance with some embodiments of the present disclosure.
Figure 3B:
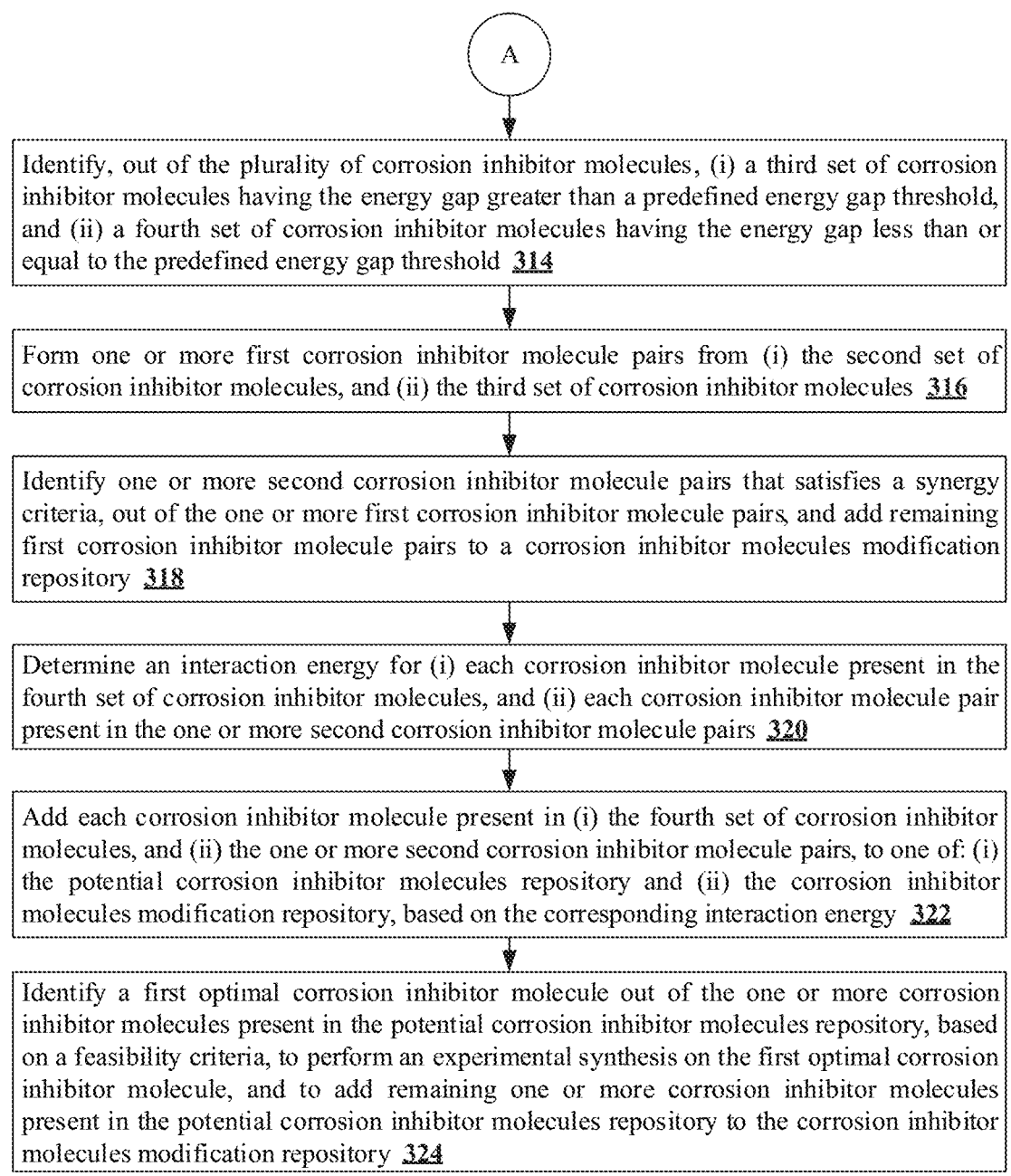

Referring collectively to FIG. 2 and FIG. 3A-3B, components and functionalities of the system 100 are described in accordance with an example embodiment of the present disclosure. For example, FIG. 2 is an exemplary block diagram illustrating modules 200 of the system 100 of FIG. 1 for screening and design of corrosion inhibitors, in accordance with some embodiments of the present disclosure. As shown in FIG. 2, the modules 200 include a molecular descriptors module 202, a quantum chemical descriptors module 204, an IE prediction module 206, and an IE checking module 208, a synergy module 210, an energy gap checking module 212, an interaction energy checking module 214, an experimental synthesis module 216, and a modification module 218. In an embodiment, the modules 200 of FIG. 2 may be stored in the plurality of modules 102a comprised in the memory 102 of the system 100.

FIG. 3A and FIG. 3B illustrates exemplary flow diagrams of a processor-implemented method 300 for screening and design of corrosion inhibitors, in accordance with some embodiments of the present disclosure. Although steps of the method 300 including process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any practical order. Further, some steps may be performed simultaneously, or some steps may be performed alone or independently.

At step 302 of the method 300, the one or more hardware processors 104 of the system 100 are configured to receive a plurality of corrosion inhibitor molecules and one or more experimental conditions for each of the plurality of corrosion inhibitor molecules. The plurality of corrosion inhibitor molecules is received from a molecular structure database. In an embodiment, the molecular structure database includes many molecules in which some may be potential inhibitor molecules and others may not. Hence the potential inhibitor molecules are identified from the molecular structure database and considered as the plurality of corrosion inhibitor molecules. The one or more experimental conditions for each of the plurality of corrosion inhibitor molecules are received from an experimental repository.

In embodiment, the one or more experimental conditions for each of the plurality of corrosion inhibitor molecules are selected from a group including but are not limited to a temperature, an inhibitor concentration, an acid concentration, an alloy composition, a pressure, a solubility, and a solution chemistry. The one or more experimental conditions of each corrosion inhibitor molecules defines the physical and chemical characteristics of the corresponding inhibitor molecule.

In an embodiment, the molecular structure database and the experimental repository may present in the repository 102b of the system 100.

At step 304 of the method 300, the one or more hardware processors 104 of the system 100 are configured to determine one or more quantum chemical descriptors for each of the plurality of corrosion inhibitor molecules received at step 302 of the method 300. In an embodiment, a quantum chemical descriptors calculating technique such as a density functional theory (DFT) technique is employed to determine the one or more quantum chemical descriptors for each corrosion inhibitor molecule. In an embodiment, the quantum chemical descriptors calculating technique may present in the quantum chemical descriptors module 204.

In an embodiment, the one or more quantum chemical descriptors for each corrosion inhibitor molecule includes a total electronic energy (E) of the corrosion inhibitor molecule, a highest occupied molecular orbital energy ($E_{HOMO}$) of the corrosion inhibitor molecule, a lowest unoccupied molecular orbital energy ($E_{LUMO}$) of the corrosion inhibitor molecule, an absolute electronegativity ($\chi$) of the of the corrosion inhibitor molecule, an electrophilicity index ($\omega$) of the corrosion inhibitor molecule, a chemical hardness ($\eta$) of the corrosion inhibitor molecule, and so on.

At step 306 of the method 300, the one or more hardware processors 104 of the system 100 are configured to determine one or more molecular descriptors for each of the plurality of corrosion inhibitor molecules received at step 302 of the method 300. In an embodiment, a molecular descriptors calculating technique such as a PaDEL-Descriptor tool, a Mordred tool, or a RDkit is employed to determine the one or more molecular descriptors for each corrosion inhibitor molecule. The molecular descriptors are numerical values that quantitatively describes the physical and chemical information of the corrosion inhibitor molecule. In an embodiment, the molecular descriptors calculating technique may present in the molecular descriptors module 202.

Figure 4:
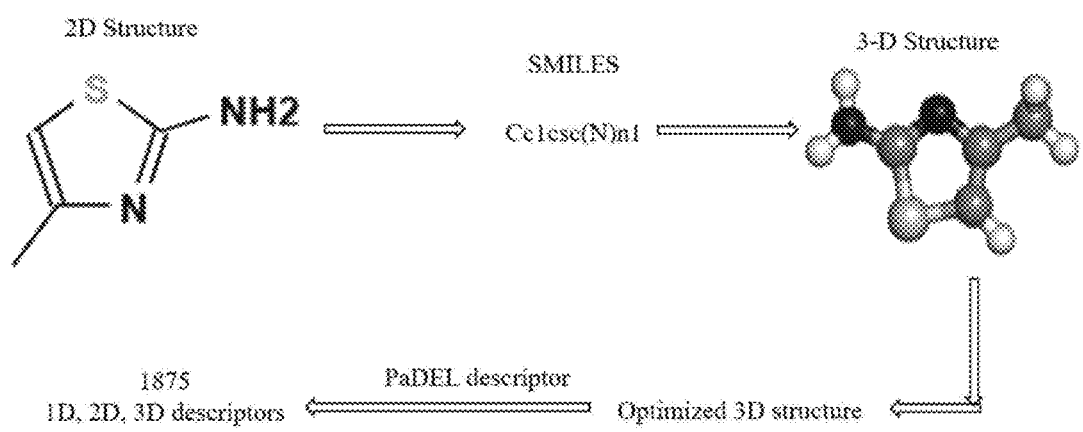
FIG. 4 shows an exemplary process flow for determining one or more molecular descriptors for each corrosion inhibitor molecule, in accordance with some embodiments of the present disclosure.

FIG. 4 shows an exemplary process flow for determining one or more molecular descriptors for each corrosion inhibitor molecule, in accordance with some embodiments of the present disclosure. As shown in FIG. 4, SMILEs notations are obtained from 2-dimensional (2-D) structure of the corrosion inhibitor molecule, using a LigParGen tool. Then, the 3-Dimensional (3-D) structure of the corrosion inhibitor molecule is obtained from the SMILEs notations, using a Obabel tool. Next, an optimized 3-D structure for the corrosion inhibitor molecule is generated by minimizing the 3-Dimensional (3-D) structure, using a genera Amber force field (GAFF) tool. Lastly, the PaDEL-Descriptor tool is used on the optimized 3-D structure to determine the one or more molecular descriptors for the corrosion inhibitor molecule.

At step 308 of the method 300, the one or more hardware processors 104 of the system 100 are configured to predict an inhibition efficiency (IE) for each of the plurality of corrosion inhibitor molecules received at step 302 of the method 300. The inhibition efficiency (IE) for each corrosion inhibitor molecule is predicted, based on the corresponding one or more molecular descriptors determined at step 306 of the method 300, and the one or more experimental conditions received at step 302 of the method 300, using an IE prediction model. In an embodiment, the IE prediction model is present in the IE prediction module 206. The IE prediction model is a deep learning-based model and obtaining the IE prediction model is detailed explained in the below steps.

At first step, a plurality of training corrosion inhibitor molecules is from the molecular structure database as mentioned at step 302 of the method. A plurality of preprocessed molecular descriptors for each of the plurality of training corrosion inhibitor molecules is received. And the one or more experimental conditions for each of the plurality of training corrosion inhibitor molecules, and the inhibition efficiency (IE) for each of the plurality of training corrosion inhibitor molecules are received from the experimental repository.

The plurality of pre-processed molecular descriptors for each training corrosion inhibitor molecule is obtained by first determining the one or more molecular descriptors for each training corrosion inhibitor molecule, using the molecular descriptors calculating technique as mentioned at step 306 of the method 300. Then, the determined one or more molecular descriptors for each training corrosion inhibitor molecule, are pre-processed to obtain the pre-processed molecular descriptors. The pre-processing includes removing the molecular descriptors having the missing values, removing the molecular descriptors having an interquartile range (IQR) (which is the difference between the $75^{th}$ and $25^{th}$ percentiles of each descriptor) of the molecular descriptors having zero and finally removing the highly correlated molecular descriptors. The highly correlated molecular descriptors are assumed to carry the redundant information and such redundancies are removed. The highly correlated molecular descriptors are identified by calculating pairwise correlation value using an equation (i):

$$r = \frac{\sum_i^n (\overline{x} - x_i)(\overline{y} - y_i)}{\sqrt{\sum_i^n (\overline{x} - x_i)^2} \sqrt{\sum_i^n (\overline{y} - y_i)^2}} \quad (1)$$

wherein r is a Pearson's correlation coefficient, x and y are two corrosion inhibitor molecules and n is a sample size (number of the one or more molecular descriptors for each training corrosion inhibitor molecule). The one of the molecular descriptor present in the pair of molecular descriptors is removed, if the r value for such pair of molecular descriptors is greater than a predefined correlation threshold value. In an embodiment, the predefined correlation threshold value is 0.95.

At second step, a multi-task network model is trained with the plurality of training corrosion inhibitor molecules, using (i) the plurality of pre-processed molecular descriptors associated with each training corrosion inhibitor molecule, (ii) the one or more experimental conditions associated with each training corrosion inhibitor molecule, and (iii) the inhibition efficiency (IE) associated with each training corrosion inhibitor molecule, to obtain the IE prediction model.

Figure 5:
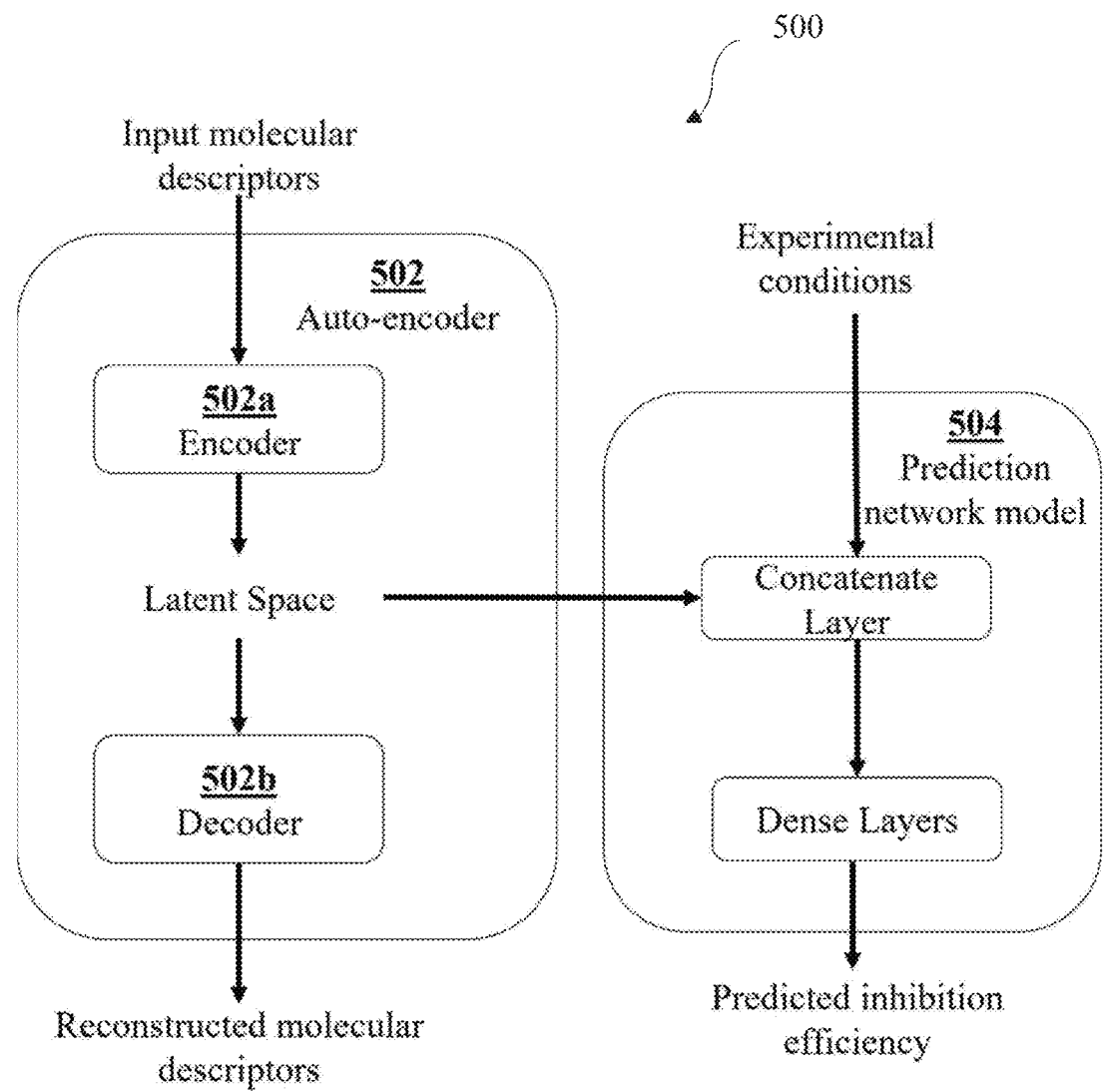
FIG. 5 is an exemplary block diagram of a multi-task network model, in accordance with some embodiments of the present disclosure.

FIG. 5 is an exemplary block diagram of a multi-task network model 500, in accordance with some embodiments of the present disclosure. As shown in FIG. 5, the multi-task network model 500 includes an auto-encoder 502 and a prediction network model 504. The auto-encoder 502 includes an encoder 502a and a decoder 502b. The encoder 502a includes a first input layer, a first dropout layer, a first dense layer, a second dropout layer, a second dense layer, a third dropout layer and a third dense layer. The decoder 502b includes a fourth dense layer, a fifth dense layer, and a six dense layer. The prediction network model 504 includes a second input layer, a concatenate layer, a seventh dense layer, an eighth dense layer, a ninth dense layer and a tenth dense layer.

The main features of the encoder 502a, the decoder 502b, and the prediction network model 504 are mentioned below:
Encoder: (128, 64, 64)
Decoder: (64, 128, 647)
Prediction Network model: (64,32,16,1)

The architecture description of the encoder 502a is mentioned below:
(i) The input layer dimension is 647.
(ii) first dropout layer, dropout rate=0.1
(iii) first dense layer, layer size=128, Relu activation
(iv) Second dropout layer, dropout rate=0.1
(v) Second dense layer, layer size=64, Relu activation
(vi) Third dropout layer, dropout rate=0.1
(vii) Third dense layer, layer size=64, Relu activation The architecture description of the decoder 502b is mentioned below:
(i) Third dense layer, layer size=64, Relu activation
(ii) Fourth dense layer, layer size=128, Relu activation
(iii) Fifth dense layer, layer size=647, linear activation, (this is the output layer, and output represent the reconstructed descriptors)

The architecture description of the prediction network model 504 is mentioned below:
(i) The second input layer-input to this are the experimental conditions
(ii) Concatenate layer—concatenate the condensed features descriptors obtained from latent space and the experimental conditions
(iii) Seventh dense layer, layer size=64, Relu activation
(iv) Eight dense layer, layer size=32, Relu activation
(v) Ninth dense layer, layer size=16, Relu activation
(vi) Tenth dense layer, layer size=1, sigmoid activation (output layer, output represent predicted inhibition efficiency)

The plurality of training corrosion inhibitor molecules is passed to the multi-task network model 500 based on a predefined batch size. The predefined batch size defines the number of training corrosion inhibitor molecules out of the plurality of training corrosion inhibitor molecules, to be passed to the multi-task network model 500, at each iteration. In an embodiment, the predefined batch size is 32, i.e. 32 training corrosion inhibitor molecules at each iteration during the training of the multi-task network model 500. The training of the multi-task network model 500 with each training corrosion inhibitor molecule is further explained in the below steps.

First, a feature vector representing the plurality of pre-processed molecular descriptors associated with the training corrosion inhibitor molecule, is passed to the encoder 502a of the auto-encoder 502, to obtain a latent feature vector of the training corrosion inhibitor molecule. Second, the latent feature vector of the training corrosion inhibitor molecule is passed to the decoder 502b of the auto-encoder 502, to obtain a reconstructed feature vector associated with the training corrosion inhibitor molecule.

Third, the one or more experimental conditions associated with the training corrosion inhibitor molecule are then concatenated with the latent feature vector of the training corrosion inhibitor molecule, to obtain a concatenated feature vector of the training corrosion inhibitor molecule. Fourth, the concatenated feature vector of the training corrosion inhibitor molecule, is then passed to the prediction network model 504, to obtain a predicted IE associated with the training corrosion inhibitor molecule.

Fifth, a cost function of the multi-task network model 504 is minimized to update the model weights of the multi-task network model. The cost function of the multi-task network model 504 is a weighted sum of an auto-encoder cost function and a prediction network model cost function. The auto-encoder cost function is defined as the mean square error (MSE) between the reconstructed feature vector associated with the training corrosion inhibitor, and the feature vector associated with the training corrosion inhibitor molecule. Similarly, the prediction network model cost function is defined as the mean square error (MSE) between the predicted IE associated with the training corrosion inhibitor molecule, and the IE associated with the training corrosion inhibitor molecule.

The cost function of the multi-task network model 500 is mathematically represented as in equation 2:

$$\text{Cost function} = \lambda_1 \text{MSE}_{prediction\ network\ model} + \lambda_2 \text{MSE}_{auto-encoder} \quad (2)$$

wherein $\lambda_1$ and $\lambda_2$ are the model weights of the prediction network model 504 and the auto-encoder 502, respectively, the $\text{MSE}_{prediction\ network\ model}$ represents the prediction network model cost function and the $\text{MSE}_{auto-encoder}$ represents the auto-encoder cost function.

The prediction network model cost function ($\text{MSE}_{prediction\ network\ model}$) is further defined as in equation 3:

$$MSE_{prediction\ network\ model} = \frac{1}{M}\sum_{i=1}^{M}(y_i - \hat{y}_i)^2 \quad (3)$$

wherein M is the number of data points, $y_i$ represents the actual IE, and $\hat{y}_i$ represents the predicted IE, and each data point refers to a set one or more molecular descriptors and the one or more experimental conditions associated with each corrosion inhibitor molecule Similarly, the auto-encoder cost function ($\text{MSE}_{auto-encoder}$) is further defined as in equation 4:

$$MSE_{auto-encoder} = \frac{1}{M}\sum_{i=1}^{M}(x_i - \hat{x}_i)^2 \quad (4)$$

wherein M is the number of data points, $x_i$ represents the actual feature vector, and $\hat{x}_i$ represents the reconstructed feature vector, and each data point refers to a set one or more molecular descriptors and the one or more experimental conditions associated with each corrosion inhibitor molecule.

Sixth and final, the model weights of the multi-task network model 500 are updated based on the value of the cost function. If the value of the cost function is less in the present iteration, compared to the value of the cost function in the previous iteration (a reference value is taken for the first iteration), then the model weights are updated with respect to the present iteration. Else the model weights are retailed as in the previous iteration.

Like these, the multi-task network model 500 is trained with the plurality of training corrosion inhibitor molecules passed in the form of the number of batches to obtain the IE prediction model.

The obtained IE prediction model is then used to predict the inhibition efficiency (IE) for each of the plurality of corrosion inhibitor molecules received at step 302 of the method 300. Predicting the inhibition efficiency (IE) for each of the plurality of corrosion inhibitor molecules, based on (i) the one or more molecular descriptors, and (ii) the one or more experimental conditions, using the IE prediction model, is further explained in the below steps.

The feature vector representing the one or more molecular descriptors associated with each of the plurality of corrosion inhibitor molecules, is passed to the encoder 502a of the auto-encoder 502 present in the IE prediction model, to obtain the latent feature vector corresponding to each of the plurality of corrosion inhibitor molecules. Then, the one or more experimental conditions corresponding to each of the plurality of corrosion inhibitor molecules are concatenated with the respective latent feature vector, to obtain the concatenated feature vector of each of the plurality of corrosion inhibitor molecules. The concatenated feature vector of each of the plurality of corrosion inhibitor molecules, is then passed to the prediction network model 504 present in the IE prediction model, to obtain the inhibition efficiency (IE) for each of the plurality of corrosion inhibitor molecules.

At step 310 of the method 300, the one or more hardware processors 104 of the system 100 are configured to determine an energy gap for each of the plurality of corrosion inhibitor molecules received at step 302 of the method 300. The energy gap for each of the plurality of corrosion inhibitor molecules is determined based on the one or more quantum chemical descriptors corresponding to the corrosion inhibitor molecule, received at step 304 of the method 300.

In an embodiment, the energy gap for each of the plurality of corrosion inhibitor molecules, is a difference between the lowest unoccupied molecular orbital energy ($E_{LUMO}$) and the highest occupied molecular orbital energy ($E_{HOMO}$) of the corrosion inhibitor molecule, i.e, $E_{LUMO} - E_{HOMO}$. The lower energy gap for the corrosion inhibitor molecule exhibits higher corrosion efficiency.

At step 312 of the method 300, the one or more hardware processors 104 of the system 100 are configured to identify (i) a first set of corrosion inhibitor molecules, and (ii) a second set of corrosion inhibitor molecules, out of the plurality of corrosion inhibitor molecules, based on the corresponding inhibition efficiency (IE) determined at step 308 of the method 300. The first set of corrosion inhibitor molecules are the corrosion inhibitor molecules having the IE greater than or equal to a predefined IE threshold. The second set of corrosion inhibitor molecules are the corrosion inhibitor molecules having the IE less than the predefined IE threshold. The greater the IE, the effective the molecules inhibit the corrosion and hence the first set of corrosion inhibitor molecules are added to a potential corrosion inhibitor molecules repository. The potential corrosion inhibitor molecules repository includes all the potential corrosion inhibitor molecules that satisfies the defined parameters for further screening. In an embodiment, the predefined IE threshold may be 90%. In an embodiment, the potential corrosion inhibitor molecules repository may present in the repository 102b of the system 100.

At step 314 of the method 300, the one or more hardware processors 104 of the system 100 are configured to identify (i) a third set of corrosion inhibitor molecules, and (ii) a fourth set of corrosion inhibitor molecules, out of the plurality of corrosion inhibitor molecules received at step 302 of the method 300, based on the corresponding energy gap determined at step 310 of the method 300. The third set of corrosion inhibitor molecules are the corrosion inhibitor molecules having the energy gap greater than a predefined energy gap threshold. The fourth set of corrosion inhibitor molecules are the corrosion inhibitor molecules having the energy gap less than or equal to the predefined energy gap threshold. As explained, the lesser the energy gap, the effective the molecule inhibits the corrosion and hence the fourth set of corrosion inhibitor molecules are directly forwarded to check an interaction energy at a later stage, through the energy gap checking module 212. In an embodiment, the predefined energy gap threshold is dynamically defined based on the energy gap of the reference inhibitor molecule known in the art.

At step 316 of the method 300, the one or more hardware processors 104 of the system 100 are configured to form one or more first corrosion inhibitor molecule pairs from (i) the second set of corrosion inhibitor molecules identified at step 312 of the method 300, and (ii) the third set of corrosion inhibitor molecules identified at step 314 of the method 300. More specifically, the corrosion inhibitor molecules present in the second set of corrosion inhibitor molecules and the third set of corrosion inhibitor molecules are first combined and all possible combinations of corrosion inhibitor molecule pairs are formed.

In an example, the number of the corrosion inhibitor molecules present in the second set of corrosion inhibitor molecules and the third set of corrosion inhibitor molecules, are 4, then the number of the first corrosion inhibitor molecule pairs formed will be 6. In another example, the number of the corrosion inhibitor molecules present in the second set of corrosion inhibitor molecules and the third set of corrosion inhibitor molecules, are 5, then the number of the first corrosion inhibitor molecule pairs formed will be 10, and so on.

At step 318 of the method 300, the one or more hardware processors 104 of the system 100 are configured to identify one or more second corrosion inhibitor molecule pairs out of the one or more first corrosion inhibitor molecule pairs formed at step 316 of the method 300. The identify one or more second corrosion inhibitor molecule pairs, are the one or more first corrosion inhibitor molecule pairs that satisfies synergy criteria. The synergy criteria defined in the synergy module 210 are used to check the synergistic effect between the two corrosion inhibitor molecules. The more the synergy the high the corrosion inhibition of the molecule.

To find out the synergistic effect between the two corrosion inhibitor molecules, the calculated HOMO ($E_{HOMO}$) and LUMO ($E_{LUMO}$) energies are plotted along with fermi energy of the metal surface. The molecule having HOMO energy closest to the fermi energy of metal will donate electron and the molecule having LUMO energy closest to the metal fermi will receive electron. While in some cases it may happen, that synergistic effect is because of impermeable monolayer formation that can be further studied by calculating an interaction energy and monolayer formation using DFT. If the computed interaction energy of mixed molecule (corrosion inhibitor molecules present in the second corrosion inhibitor pair) is more than the sum of the interaction energy of the individual molecule then there is synergy between the two such corrosion inhibitor molecules.

Further, the one or more first corrosion inhibitor molecule pairs those does not satisfy the synergy criteria are to a corrosion inhibitor molecules modification repository. In an embodiment, the corrosion inhibitor molecules modification repository may present in the repository 102b of the system 100.

At step 320 of the method 300, the one or more hardware processors 104 of the system 100 are configured to determine an interaction energy for (i) each corrosion inhibitor molecule present in the fourth set of corrosion inhibitor molecules, and (ii) each corrosion inhibitor molecule pair present in the one or more second corrosion inhibitor molecule pairs. The interaction energy for each corrosion inhibitor molecule pair is the sum of the interaction energies of the corrosion inhibitor molecules present in the corresponding corrosion inhibitor molecule pair. In an embodiment, the interaction energy for each corrosion inhibitor molecule is determined using one of: the DFT technique, a molecular dynamics (MD) technique, and a reactive force field (ReaxFF) technique.

At step 322 of the method 300, the one or more hardware processors 104 of the system 100 are configured to add each corrosion inhibitor molecule present in the fourth set of corrosion inhibitor molecules, to one of: (i) the potential corrosion inhibitor molecules repository and (ii) the corrosion inhibitor molecules modification repository, based on the corresponding interaction energy of each corrosion inhibitor molecule, through the interaction energy checking module 214. More particularly, the corrosion inhibitor molecules present in the fourth set of corrosion inhibitor molecules, having the interaction energy greater than or equal to a predefined interaction energy threshold, are added to the potential corrosion inhibitor molecules repository. Similarly, the corrosion inhibitor molecules present in the fourth set of corrosion inhibitor molecules, having the interaction energy less than the predefined interaction energy threshold, are added to the corrosion inhibitor molecules modification repository. In an embodiment, the predefined interaction energy threshold is dynamically defined based on the interaction energy of the reference inhibitor molecule known in the art.

Further, at step 322 of the method 300, the one or more hardware processors 104 of the system 100 are configured to add each corrosion inhibitor molecule present in the one or more second corrosion inhibitor molecule pairs, to one of: (i) the potential corrosion inhibitor molecules repository and (ii) the corrosion inhibitor molecules modification repository, based on the corresponding interaction energy.

More particularly, the corrosion inhibitor molecules present in the second corrosion inhibitor molecule pair whose interaction energy is greater than or equal to a predefined interaction energy pair threshold, are added to the potential corrosion inhibitor molecules repository. Similarly, the corrosion inhibitor molecules present in the second corrosion inhibitor molecule pair whose interaction energy is less than the predefined interaction energy pair threshold, are added to the corrosion inhibitor molecules modification repository. In an embodiment, the predefined interaction energy pair threshold is a value that is greater than the interaction energy of each individual inhibitor molecule present in the second corrosion inhibitor molecule pair.

At step 324 of the method 300, the one or more hardware processors 104 of the system 100 are configured to identify a first optimal corrosion inhibitor molecule out of the one or more corrosion inhibitor molecules present in the potential corrosion inhibitor molecules repository, based on feasibility criteria. The feasibility criteria define how feasible the corrosion inhibitor molecule is. In an embodiment, the feasibility criteria include at least one of: (i) how biodegradable or green molecule (eco-friendly), (ii) abundantly available, and (iii) less cost or cheap. Based on the feasibility criteria, the first optimal corrosion inhibitor molecule is identified. Then, an experimental synthesis is carried out on the first optimal corrosion inhibitor molecule, to a synthesized corrosion inhibitor molecule.

Further, the corrosion inhibition efficiency of the synthesized corrosion inhibitor molecule is calculated using a weight loss technique and by comparing with a reference corrosion inhibitor molecule, through the experimental synthesis module. If the corrosion inhibition efficiency of the synthesized corrosion inhibitor molecule, is more than the corrosion inhibition efficiency of the reference molecule, then such synthesized corrosion inhibitor molecule is proceeded towards plant trails. If the corrosion inhibition efficiency of the synthesized corrosion inhibitor molecule, is less than or equal to the corrosion inhibition efficiency of the reference molecule, then the synthesized corrosion inhibitor molecule is added to the corrosion inhibitor molecules modification repository. In this case, the next corrosion inhibition molecule present in the potential corrosion inhibitor molecules repository, that most satisfies the feasibility criteria is identified as the first optimal corrosion inhibitor molecule and the process is continued until one such first optimal corrosion inhibitor molecule is identified for the plant trails.

The remaining one or more corrosion inhibitor molecules present in the potential corrosion inhibitor molecules repository, that does not satisfy the feasibility criteria, are added to the corrosion inhibitor molecules modification repository.

The one or more hardware processors 104 of the system 100 are configured to perform plant trails using the first optimal corrosion inhibitor molecule identified at step 324 of the method 300. The purpose of the plant trial in to test the first optimal corrosion inhibitor molecule (or combination of the molecules in case of synergy) in the actual conditions such as temperature, pressure, acidity/alkalinity, and flow conditions, etc. If the molecule (or combination of molecules in case of synergy) shows better inhibition efficiency, then it goes for industrial scale use, else the molecule is again added to the corrosion inhibitor molecules modification repository.

The one or more hardware processors 104 of the system 100 are further configured to identify a second optimal corrosion inhibitor molecule out of the one or more corrosion inhibitor molecules present in the corrosion inhibitor molecules modification repository, based on the feasibility criteria defined at step 324 of the method 300.

Further, the one or more hardware processors 104 of the system 100 are configured to identify a second optimal corrosion inhibitor molecule out of the one or more corrosion inhibitor, and perform modifications to the second optimal corrosion inhibitor molecule, through the modification module 218, to obtain a modified corrosion inhibitor molecule. The modified corrosion inhibitor molecule is then added to the plurality of corrosion inhibitor molecules as received at the step 302 of the method 300, for further screening and design of corrosion inhibitors. The purpose of obtaining the modified corrosion inhibitor molecule is to get the corrosion inhibitor molecule that is suitable for the application.

The steps for performing the modifications to the second optimal corrosion inhibitor molecule, to obtain the modified corrosion inhibitor molecule, is explained below in detail.

First, xyz-coordinates of the second optimal corrosion inhibitor molecule is determined using a coordinates determination model such as an AVOGADRO tool, a LIGPARGEN tool, and so on. Second, the one or more locations having atoms for the second optimal corrosion inhibitor molecule where the modifications to be performed, based on the determined xyz-coordinates. Third, an atom present in each location of the one or more locations in the second optimal corrosion inhibitor molecule, is replaced with a functional group selected from one or more functional groups present in a functional group repository. Fourth and last, the replaced functional groups in the second optimal corrosion inhibitor molecule are rotated and adjusted in such a way that a distance between the atoms of the replaced functional groups and the existing atoms in the second optimal corrosion inhibitor molecule should be greater than a sum of covalent radii of the atoms, to obtain the modified corrosion inhibitor molecule. In an embodiment, the functional group repository is present in the repository 102b of the system 100.

Figure 6:
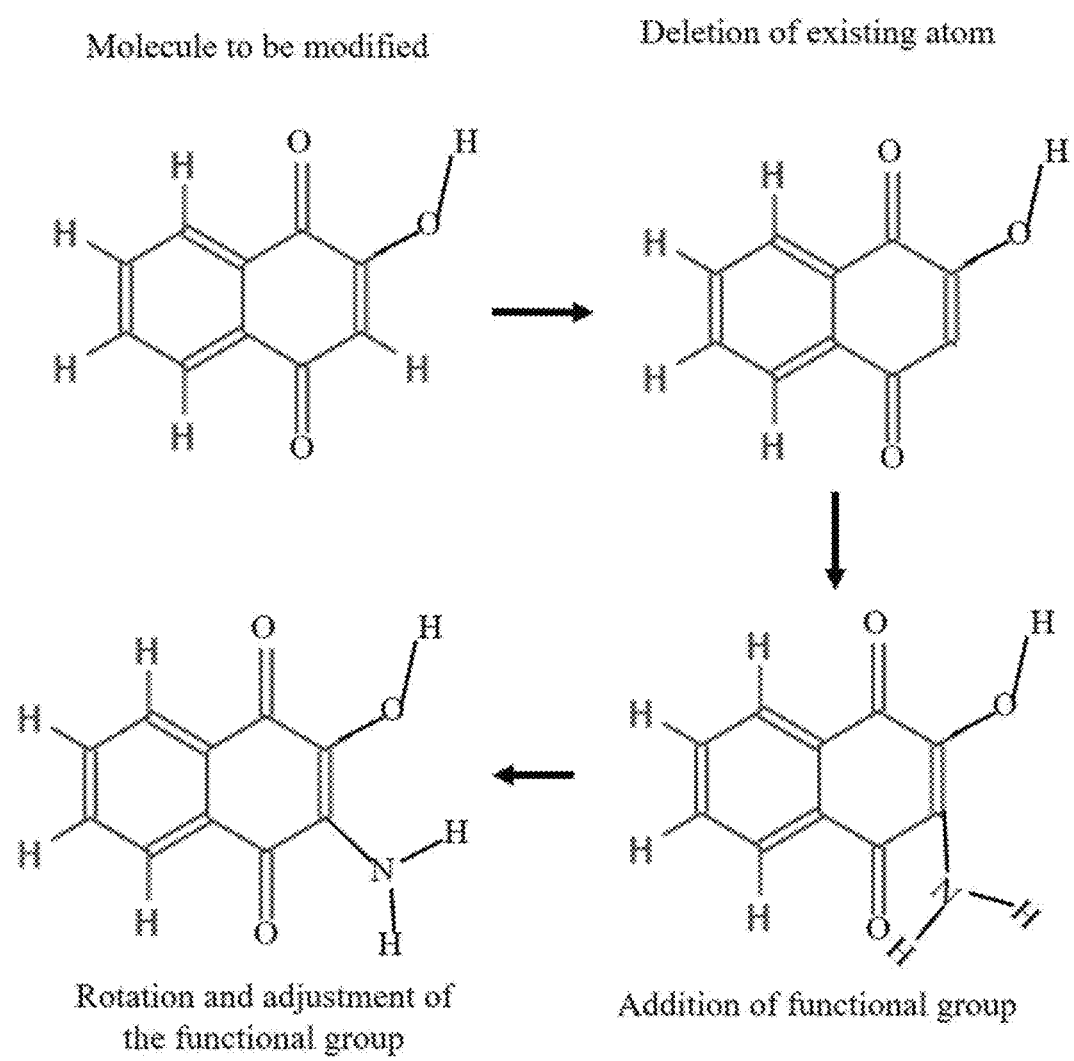
FIG. 6 shows an exemplary process flow for obtaining an exemplary modified corrosion inhibitor molecule, in accordance with some embodiments of the present disclosure.

FIG. 6 shows an exemplary process flow for obtaining an exemplary modified corrosion inhibitor molecule, in accordance with some embodiments of the present disclosure. In FIG. 6, the molecule 2-hydroxy-1,4-naphthaquinone (called as lawsone) is modified to get the modified corrosion inhibitor molecule with the enhanced corrosion inhibition efficiency. The xyz-coordinates of the lawsone molecule is obtained using the AVOGADRO tool. The locations to introduce the modification are identified i.e., H-atom between C=O and —OH group and deleted from the xyz-coordinates. The —NH2 amine functional group selected from the functional group repository and introduced in place of H— atom deleted in the previous step. Further, the functional group (—NH2) is adjusted and rotated in order to avoid overlap or any other unintended bond formation. Thus, the lawsone molecule is modified into 2-hydroxy-3-amino-1,4-naphthaquinone which is again added to plurality of corrosion inhibitors for further screening.

The method and systems of the present disclosure ensures to predict the inhibition efficiency (IE) of the molecule accurately, as the disclosed IE prediction model of the present disclosure is developed by training a multi-task network model using the molecular descriptors of different classes of the molecules, and also the experimental conditions of the molecule. Further, the present disclosure provides the unique screening technique that screens the molecules not only based on the molecular descriptors (for finding the IE), but also using quantum chemical descriptors, and using various parameters including the inhibition efficiency of the molecule, an energy gap of the molecule, a synergistic effect of the molecules and an interaction energy of the molecules. Hence the molecules screened using the unique screening technique, may be efficient and effective for the corrosion inhibition end applications. Further the present disclosure allows to design the new corrosion inhibition molecules by making changes to the molecules that suits based on the end applications.

Example Scenario

The corrosion data from literature and information available in the public domain is collected to build the dataset of corrosion inhibitors for mild steel in hydrochloric acid. The build dataset is the largest dataset having 135 organic corrosion inhibitors across multiple classes such as pyridine, imidazole, Schiff bases, trizaole, thiol, amine, thiazole, hydrazone, etc. The data collected includes experimental inhibition efficiencies at different temperatures, inhibitor concentrations and acid concentrations obtained from weight loss, Tafel polarization and electrochemical impedance spectroscopy (EIS) methods.

The unprocessed corrosion data consists of 700 and 1875 columns of molecular descriptors apart from experimental conditions. After missing data analysis, the molecular descriptors are reduced to 1496. Further, after IQR analysis, the number of molecular descriptors is reduced to 1327 and following removal of highly correlated descriptors, the count is further reduced to 647. Hence, after data pre-processing, 647 molecular descriptors out of the original 1875 descriptors are the pre-processed molecular descriptors.

With 647 molecular descriptors, conventional machine learning models such as Linear regression, lasso regression, ridge regression], random forest, along with the multi-task network model of the present disclosure. For the conventional machine learning models, the experimental conditions are incorporated as input features along with molecular descriptors. In the multi-task network model of the present disclosure, the dimensionality of molecular descriptors is reduced from 647 to 64 using auto-encoder and learned encodings in the latent space are fed to the prediction network model. Table 1 and Table 2 show the optimized hyper-parameters and the performance of the conventional machine learning models and the multi-task network model of the present disclosure, respectively.

TABLE 1

| Model | Optimal values of hyper-parameters |
| --- | --- |
| Linear | No hyper-parameter |
| Ridge | $\lambda = 1.12E{-}06$ |
| Lasso | $\lambda = 0.003069$ |
| Random forest | N_estimators = 50, max_features = 'auto', min_samples_split = 2, min_samples_leaf = 1, Bootstrap = 'True' |
| multi-task network model | batch size = 32, dropout rate = 0.1, $\lambda_1 = 1$, $\lambda_2 = 50$, epochs = 2500 |

TABLE 2

| Model | Train MAE | Validation MAE | Test MAE |
| --- | --- | --- | --- |
| Linear | 7.77 | 4.8E+10 | 2.1E+11 |
| Ridge | 7.77 | 10.92 | 10.78 |
| Lasso | 7.79 | 10.85 | 10.75 |
| Random forest | 2.82 | 6.74 | 7.06 |
| multi-task network model | 1.96 | 5.03 | 6.46 |

As shown in Table 2, the multi-task network model of the present disclosure performed the best compared to the conventional machine learning models. The MAE value on test data was found to be 6.46.

The embodiments of present disclosure herein address unresolved problem of the screening the corrosion inhibitor molecules based on various parameters including the accurate inhibition efficiency of the molecule and using the unique screening technique. The experimental results also show that the IE prediction model of the present disclosure outperform in predicting the inhibition efficiency of the molecule, compared to the conventional machine learning models in the art.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method for screening and design of corrosion inhibitors, the method comprising the steps of:
   receiving, via one or more hardware processors, a plurality of corrosion inhibitor molecules from a molecular structure database, and one or more experimental conditions for each of the plurality of corrosion inhibitor molecules from an experimental repository;
   determining, via the one or more hardware processors, one or more quantum chemical descriptors for each of the plurality of corrosion inhibitor molecules, using a quantum chemical descriptors calculating technique;
   determining, via the one or more hardware processors, one or more molecular descriptors for each of the plurality of corrosion inhibitor molecules, using a molecular descriptors calculating technique;
   predicting, via the one or more hardware processors, an inhibition efficiency (IE) for each of the plurality of corrosion inhibitor molecules, based on (i) the one or more molecular descriptors, and (ii) the one or more experimental conditions, using an IE prediction model;
   determining, via the one or more hardware processors, an energy gap for each of the plurality of corrosion inhibitor molecules, based on the one or more quantum chemical descriptors for each of the plurality of corrosion inhibitor molecules;
   identifying, via the one or more hardware processors, out of the plurality of corrosion inhibitor molecules, (i) a first set of corrosion inhibitor molecules having the IE greater than or equal to a predefined IE threshold, and (ii) a second set of corrosion inhibitor molecules having the IE less than the predefined IE threshold, and adding the first set of corrosion inhibitor molecules to a potential corrosion inhibitor molecules repository;
   identifying, via the one or more hardware processors, out of the plurality of corrosion inhibitor molecules, (i) a third set of corrosion inhibitor molecules having the energy gap greater than a predefined energy gap threshold, and (ii) a fourth set of corrosion inhibitor molecules having the energy gap less than or equal to the predefined energy gap threshold;
   forming, via the one or more hardware processors, one or more first corrosion inhibitor molecule pairs from (i) the second set of corrosion inhibitor molecules, and (ii) the third set of corrosion inhibitor molecules;
   identifying, via the one or more hardware processors, one or more second corrosion inhibitor molecule pairs that satisfies a synergy criterion out of the one or more first corrosion inhibitor molecule pairs, and to add remaining first corrosion inhibitor molecule pairs to a corrosion inhibitor molecules modification repository;
   determining, via the one or more hardware processors, an interaction energy for (i) each corrosion inhibitor molecule present in the fourth set of corrosion inhibitor molecules, and (ii) each corrosion inhibitor molecule pair present in the one or more second corrosion inhibitor molecule pairs;
   adding, via the one or more hardware processors, each corrosion inhibitor molecule present in (i) the fourth set of corrosion inhibitor molecules, and (ii) the one or more second corrosion inhibitor molecule pairs, to one of: (i) the potential corrosion inhibitor molecules repository and (ii) the corrosion inhibitor molecules modification repository, based on the corresponding interaction energy; and
   identifying, via the one or more hardware processors, a first optimal corrosion inhibitor molecule out of the one or more corrosion inhibitor molecules present in the potential corrosion inhibitor molecules repository, based on a feasibility criteria, to perform an experimental synthesis on the first optimal corrosion inhibitor molecule, and to add remaining one or more corrosion inhibitor molecules present in the potential corrosion inhibitor molecules repository to the corrosion inhibitor molecules modification repository.

2. The method of claim 1, further comprising:
   identifying, via the one or more hardware processors, a second optimal corrosion inhibitor molecule out of the one or more corrosion inhibitor molecules present in the corrosion inhibitor molecules modification repository, based on the feasibility criteria; and
   performing, via the one or more hardware processors, modifications to the second optimal corrosion inhibitor molecule, to obtain a modified corrosion inhibitor molecule, and adding the modified corrosion inhibitor molecule to the plurality of corrosion inhibitor molecules, for further screening and design of corrosion inhibitors.

3. The method of claim 2, wherein performing the modifications to the second optimal corrosion inhibitor molecule, to obtain the modified corrosion inhibitor molecule, comprises:
   determining xyz-coordinates of the second optimal corrosion inhibitor molecule using a coordinates determination model;
   identifying one or more locations having atoms for the second optimal corrosion inhibitor molecule where the modifications to be performed, based on the xyz-coordinates;
   replacing an atom present in each location of the one or more locations in the second optimal corrosion inhibitor molecule, with a functional group identified from one or more functional groups; and
   rotating and adjusting the replaced functional groups in the second optimal corrosion inhibitor molecule in such a way that a distance between the atoms of the replaced functional groups and the existing atoms in the second optimal corrosion inhibitor molecule should be greater than a sum of covalent radii of the atoms, to obtain the modified corrosion inhibitor molecule.

4. The method of claim 1, further comprising:
   performing, via the one or more hardware processors, plant trails on the first optimal corrosion inhibitor molecule.

5. The method of claim 1, wherein the IE prediction model is obtained by:
   receiving (i) a plurality of training corrosion inhibitor molecules from the molecular structure database, (ii) a plurality of pre-processed molecular descriptors for each of the plurality of training corrosion inhibitor molecules, (iii) the one or more experimental conditions for each of the plurality of training corrosion inhibitor molecules, from the experimental repository and (iv) the inhibition efficiency (IE) for each of the plurality of training corrosion inhibitor molecules from the experimental repository; and
   training a multi-task network model comprising an autoencoder and a prediction network model, with the plurality of training corrosion inhibitor molecules based on a batch size, using (i) the plurality of pre-processed molecular descriptors associated with each training corrosion inhibitor molecule, (ii) the one or more experimental conditions associated with each training corrosion inhibitor molecule, and (iii) the inhibition efficiency (IE) associated with each training corrosion inhibitor molecule, to obtain the IE prediction model, wherein training the multi-task network model with each training corrosion inhibitor molecule comprising:

passing a feature vector of the plurality of pre-processed molecular descriptors associated with the training corrosion inhibitor molecule, to an encoder of the auto-encoder, to obtain a latent feature vector of the training corrosion inhibitor molecule;

passing the latent feature vector of the training corrosion inhibitor molecule, to a decoder of the auto-encoder, to obtain a reconstructed feature vector associated with the training corrosion inhibitor molecule;

concatenating the one or more experimental conditions associated with the training corrosion inhibitor molecule with the latent feature vector of the training corrosion inhibitor molecule, to obtain a concatenated feature vector of the training corrosion inhibitor molecule;

passing the concatenated feature vector of the training corrosion inhibitor molecule, to the prediction network model, to obtain a predicted IE associated with the training corrosion inhibitor molecule;

minimizing the cost function of the multi-task network model, wherein the cost function is a weighted sum of an auto-encoder cost function and a prediction network model cost function; and updating model weights of the multi-task network model, based on the cost function.

6. The method of claim 5, wherein:
the auto-encoder cost function is defined as the mean square error between the reconstructed feature vector associated with the training corrosion inhibitor, and the feature vector associated with the training corrosion inhibitor molecule; and
the prediction network model cost function is defined as the mean square error between the predicted IE associated with the training corrosion inhibitor molecule, and the IE associated with the training corrosion inhibitor molecule.

7. The method of claim 1, wherein predicting the inhibition efficiency (IE) for each of the plurality of corrosion inhibitor molecules, based on (i) the one or more molecular descriptors, and (ii) the one or more experimental conditions, using the IE prediction model, comprising;

passing a feature vector of the one or more molecular descriptors associated with each of the plurality of corrosion inhibitor molecules, to an encoder of an auto-encoder present in the IE prediction model, to obtain a latent feature vector corresponding to each of the plurality of corrosion inhibitor molecules;

concatenating the one or more experimental conditions for each of the plurality of corrosion inhibitor molecules with the latent feature vector corresponding to each of the plurality of corrosion inhibitor molecules, to obtain a concatenated feature vector of each of the plurality of corrosion inhibitor molecules; and passing the concatenated feature vector of each of the plurality of corrosion inhibitor molecules, to a prediction network model present in the IE prediction model, to obtain the inhibition efficiency (IE) for each of the plurality of corrosion inhibitor molecules.

8. The method of claim 1, wherein the one or more experimental conditions are selected from a group comprising but are not limited to: (i) a temperature, (ii) an inhibitor concentration, (iii) an acid concentration, (iv) an alloy composition, (v) a pressure, (vi) a solubility, and (vii) a solution chemistry.

9. A system for screening and design of corrosion inhibitors, the system comprising:
a memory storing instructions;
one or more Input/Output (I/O) interfaces; and
one or more hardware processors coupled to the memory via the one or more I/O interfaces, wherein the one or more hardware processors are configured by the instructions to:
receive a plurality of corrosion inhibitor molecules from a molecular structure database, and one or more experimental conditions for each of the plurality of corrosion inhibitor molecules from an experimental repository;
determine one or more quantum chemical descriptors for each of the plurality of corrosion inhibitor molecules, using a quantum chemical descriptors calculating technique;
determine one or more molecular descriptors for each of the plurality of corrosion inhibitor molecules, using a molecular descriptors calculating technique;
predict an inhibition efficiency (IE) for each of the plurality of corrosion inhibitor molecules, based on (i) the one or more molecular descriptors, and (ii) the one or more experimental conditions, using an IE prediction model;
determine an energy gap for each of the plurality of corrosion inhibitor molecules, based on the one or more quantum chemical descriptors for each of the plurality of corrosion inhibitor molecules;
identify, out of the plurality of corrosion inhibitor molecules, (i) a first set of corrosion inhibitor molecules having the IE greater than or equal to a predefined IE threshold, and (ii) a second set of corrosion inhibitor molecules having the IE less than the predefined IE threshold, and adding the first set of corrosion inhibitor molecules to a potential corrosion inhibitor molecules repository;
identify, out of the plurality of corrosion inhibitor molecules, (i) a third set of corrosion inhibitor molecules having the energy gap greater than a predefined energy gap threshold, and (ii) a fourth set of corrosion inhibitor molecules having the energy gap less than or equal to the predefined energy gap threshold;
form one or more first corrosion inhibitor molecule pairs from (i) the second set of corrosion inhibitor molecules, and (ii) the third set of corrosion inhibitor molecules;
identify one or more second corrosion inhibitor molecule pairs that satisfies a synergy criteria, out of the one or more first corrosion inhibitor molecule pairs, and add remaining first corrosion inhibitor molecule pairs to a corrosion inhibitor molecules modification repository;
determine an interaction energy for (i) each corrosion inhibitor molecule present in the fourth set of corrosion inhibitor molecules, and (ii) each corrosion inhibitor molecule pair present in the one or more second corrosion inhibitor molecule pairs;
add each corrosion inhibitor molecule present in (i) the fourth set of corrosion inhibitor molecules, and (ii) the one or more second corrosion inhibitor molecule pairs, to one of: (i) the potential corrosion inhibitor molecules repository and (ii) the corrosion inhibitor molecules modification repository, based on the corresponding interaction energy; and identify a first optimal corrosion inhibitor molecule out of the one or more corrosion inhibitor molecules present in the potential corrosion inhibitor molecules repository, based on a feasibility criteria, to perform an experimental synthesis on the first optimal corrosion inhibitor molecule, and to add remaining one or more corrosion inhibitor molecules present in the potential corrosion inhibitor molecules repository to the corrosion inhibitor molecules modification repository.

10. The system of claim 9, wherein the one or more hardware processors are further configured to:

identify a second optimal corrosion inhibitor molecule out of the one or more corrosion inhibitor molecules present in the corrosion inhibitor molecules modification repository, based on the feasibility criteria; and perform modifications to the second optimal corrosion inhibitor molecule, to obtain a modified corrosion inhibitor molecule, and adding the modified corrosion inhibitor molecule to the plurality of corrosion inhibitor molecules, for further screening and design of corrosion inhibitors.

11. The system of claim 10, wherein the one or more hardware processors are configured to perform the modifications to the second optimal corrosion inhibitor molecule, to obtain the modified corrosion inhibitor molecule, by:

determining xyz-coordinates of the second optimal corrosion inhibitor molecule using a coordinates determination model;

identifying one or more locations having atoms for the second optimal corrosion inhibitor molecule where the modifications to be performed, based on the xyz-coordinates;

replacing an atom present in each location of the one or more locations in the second optimal corrosion inhibitor molecule, with a functional group identified from one or more functional groups; and rotating and adjusting the replaced functional groups in the second optimal corrosion inhibitor molecule in such a way that a distance between the atoms of the replaced functional groups and the existing atoms in the second optimal corrosion inhibitor molecule should be greater than a sum of covalent radii of the atoms, to obtain the modified corrosion inhibitor molecule.

12. The system of claim 9, wherein the one or more hardware processors are further configured to perform plant trails on the first optimal corrosion inhibitor molecule.

13. The system of claim 9, wherein the one or more hardware processors are configured to obtain the IE prediction model, by:

receiving (i) a plurality of training corrosion inhibitor molecules from the molecular structure database, (ii) a plurality of pre-processed molecular descriptors for each of the plurality of training corrosion inhibitor molecules, (iii) the one or more experimental conditions for each of the plurality of training corrosion inhibitor molecules, from the experimental repository and (iv) the inhibition efficiency (IE) for each of the plurality of training corrosion inhibitor molecules from the experimental repository; and training a multi-task network model comprising an auto-encoder and a prediction network model, with the plurality of training corrosion inhibitor molecules based on a batch size, using (i) the plurality of pre-processed molecular descriptors associated with each training corrosion inhibitor molecule, (ii) the one or more experimental conditions associated with each training corrosion inhibitor molecule, and (iii) the inhibition efficiency (IE) associated with each training corrosion inhibitor molecule, to obtain the IE prediction model, wherein training the multi-task network model with each training corrosion inhibitor molecule comprising:

passing a feature vector of the plurality of pre-processed molecular descriptors associated with the training corrosion inhibitor molecule, to an encoder of the auto-encoder, to obtain a latent feature vector of the training corrosion inhibitor molecule;

passing the latent feature vector of the training corrosion inhibitor molecule, to a decoder of the auto-encoder, to obtain a reconstructed feature vector associated with the training corrosion inhibitor molecule;

concatenating the one or more experimental conditions associated with the training corrosion inhibitor molecule with the latent feature vector of the training corrosion inhibitor molecule, to obtain a concatenated feature vector of the training corrosion inhibitor molecule;

passing the concatenated feature vector of the training corrosion inhibitor molecule, to the prediction network model, to obtain a predicted IE associated with the training corrosion inhibitor molecule;

minimizing the cost function of the multi-task network model, wherein the cost function is a weighted sum of an auto-encoder cost function and a prediction network model cost function; and updating model weights of the multi-task network model, based on the cost function.

14. The system of claim 13, wherein:

the auto-encoder cost function is defined as the mean square error between the reconstructed feature vector associated with the training corrosion inhibitor, and the feature vector associated with the training corrosion inhibitor molecule; and the prediction network model cost function is defined as the mean square error between the predicted IE associated with the training corrosion inhibitor molecule, and the IE associated with the training corrosion inhibitor molecule.

15. The system of claim 9, wherein the one or more hardware processors are configured to predict the inhibition efficiency (IE) for each of the plurality of corrosion inhibitor molecules, based on (i) the one or more molecular descriptors, and (ii) the one or more experimental conditions, using the IE prediction model, by;

passing a feature vector of the one or more molecular descriptors associated with each of the plurality of corrosion inhibitor molecules, to an encoder of an auto-encoder present in the IE prediction model, to obtain a latent feature vector corresponding to each of the plurality of corrosion inhibitor molecules;

concatenating the one or more experimental conditions for each of the plurality of corrosion inhibitor molecules with the latent feature vector corresponding to each of the plurality of corrosion inhibitor molecules, to obtain a concatenated feature vector of each of the plurality of corrosion inhibitor molecules; and passing the concatenated feature vector of each of the plurality of corrosion inhibitor molecules, to a prediction network model present in the IE prediction model, to obtain the inhibition efficiency (IE) for each of the plurality of corrosion inhibitor molecules.

16. The system of claim 9, wherein the one or more experimental conditions are selected from a group comprising but are not limited to: (i) a temperature, (ii) an inhibitor concentration, (iii) an acid concentration, (iv) an alloy composition, (v) a pressure, (vi) a solubility, and (vii) a solution chemistry.

17. One or more non-transitory machine-readable information storage mediums comprising one or more instructions which when executed by one or more hardware processors cause:
  receiving, a plurality of corrosion inhibitor molecules from a molecular structure database, and one or more experimental conditions for each of the plurality of corrosion inhibitor molecules from an experimental repository;
  determining, one or more quantum chemical descriptors for each of the plurality of corrosion inhibitor molecules, using a quantum chemical descriptors calculating technique;
  determining, one or more molecular descriptors for each of the plurality of corrosion inhibitor molecules, using a molecular descriptors calculating technique;
  predicting, an inhibition efficiency (IE) for each of the plurality of corrosion inhibitor molecules, based on (i) the one or more molecular descriptors, and (ii) the one or more experimental conditions, using an IE prediction model;
  determining, an energy gap for each of the plurality of corrosion inhibitor molecules, based on the one or more quantum chemical descriptors for each of the plurality of corrosion inhibitor molecules;
  identifying, out of the plurality of corrosion inhibitor molecules, (i) a first set of corrosion inhibitor molecules having the IE greater than or equal to a predefined IE threshold, and (ii) a second set of corrosion inhibitor molecules having the IE less than the predefined IE threshold, and adding the first set of corrosion inhibitor molecules to a potential corrosion inhibitor molecules repository;
  identifying out of the plurality of corrosion inhibitor molecules, (i) a third set of corrosion inhibitor molecules having the energy gap greater than a predefined energy gap threshold, and (ii) a fourth set of corrosion inhibitor molecules having the energy gap less than or equal to the predefined energy gap threshold;
  forming, one or more first corrosion inhibitor molecule pairs from (i) the second set of corrosion inhibitor molecules, and (ii) the third set of corrosion inhibitor molecules;
  identifying, one or more second corrosion inhibitor molecule pairs that satisfies a synergy criterion out of the one or more first corrosion inhibitor molecule pairs, and to add remaining first corrosion inhibitor molecule pairs to a corrosion inhibitor molecules modification repository;
  determining, an interaction energy for (i) each corrosion inhibitor molecule present in the fourth set of corrosion inhibitor molecules, and (ii) each corrosion inhibitor molecule pair present in the one or more second corrosion inhibitor molecule pairs;
  adding, each corrosion inhibitor molecule present in (i) the fourth set of corrosion inhibitor molecules, and (ii) the one or more second corrosion inhibitor molecule pairs, to one of: (i) the potential corrosion inhibitor molecules repository and (ii) the corrosion inhibitor molecules modification repository, based on the corresponding interaction energy;
  identifying, a first optimal corrosion inhibitor molecule out of the one or more corrosion inhibitor molecules present in the potential corrosion inhibitor molecules repository, based on a feasibility criteria, to perform an experimental synthesis on the first optimal corrosion inhibitor molecule, and to add remaining one or more corrosion inhibitor molecules present in the potential corrosion inhibitor molecules repository to the corrosion inhibitor molecules modification repository;
  identifying, a second optimal corrosion inhibitor molecule out of the one or more corrosion inhibitor molecules present in the corrosion inhibitor molecules modification repository, based on the feasibility criteria;
  performing, modifications to the second optimal corrosion inhibitor molecule, to obtain a modified corrosion inhibitor molecule, and adding the modified corrosion inhibitor molecule to the plurality of corrosion inhibitor molecules, for further screening and design of corrosion inhibitors; and
  performing, plant trails on the first optimal corrosion inhibitor molecule.

* * * * *